United States Patent
Ray

(10) Patent No.: US 10,161,736 B2
(45) Date of Patent: *Dec. 25, 2018

(54) PRINTED STRETCH SENSOR

(71) Applicant: Xerox Corporation, Norwalk, CT (US)

(72) Inventor: Elton T. Ray, Livonia, NY (US)

(73) Assignee: Xerox Corporation, Norwalk, CT (US)

(*) Notice: Subject to any disclaimer, the term of this patent is extended or adjusted under 35 U.S.C. 154(b) by 147 days.

This patent is subject to a terminal disclaimer.

(21) Appl. No.: 15/159,030

(22) Filed: May 19, 2016

(65) Prior Publication Data

US 2016/0265897 A1    Sep. 15, 2016

Related U.S. Application Data

(63) Continuation of application No. 13/566,726, filed on Aug. 3, 2012, now abandoned.

(51) Int. Cl.
| | | |
|---|---|---|
| G01B 7/16 | (2006.01) | |
| G01L 1/20 | (2006.01) | |
| G06F 3/041 | (2006.01) | |
| G06F 3/047 | (2006.01) | |
| G01D 5/16 | (2006.01) | |
| G01N 27/04 | (2006.01) | |
| G01G 3/14 | (2006.01) | |

(52) U.S. Cl.
CPC ............... *G01B 7/20* (2013.01); *G01D 5/16* (2013.01); *G01L 1/205* (2013.01); *G06F 3/047* (2013.01); *G06F 3/0414* (2013.01); *G01G 3/14* (2013.01); *G01N 27/041* (2013.01)

(58) Field of Classification Search
CPC .. G01B 7/20; G01D 5/16; G01L 1/205; G06F 3/0414; G06F 3/047
See application file for complete search history.

(56) References Cited

U.S. PATENT DOCUMENTS

| | | | | |
|---|---|---|---|---|
| 3,993,842 | A * | 11/1976 | Hirsch | C09D 5/24 252/509 |
| 5,086,785 | A * | 2/1992 | Gentile | A61B 5/1126 338/210 |
| 2012/0053424 | A1* | 3/2012 | Kenalty | A61B 5/0015 600/300 |
| 2016/0265896 | A1* | 9/2016 | Ray | G01L 1/205 |

OTHER PUBLICATIONS

The Condensed Chemical Dictionary, Revised by Gessner G. Hawley, Van Rostrand Reinhold Company, Tenth Edition, Apr. 1981, p. 709.
Principles of Polymerization, George Odian, Wiley Interscience, New York, Second Edition, 1981, pp. 32-37.

* cited by examiner

*Primary Examiner* — Hezron E Williams
*Assistant Examiner* — David Z Huang
(74) *Attorney, Agent, or Firm* — Marylou J. Lavoie, Esq. LLC

(57) ABSTRACT

Disclosed is a patterned article comprising: (1) a deformable nonconductive substrate; (2) an imagewise pattern thereon of a conductive stretchable ink; and (3) an external circuit connecting the imagewise pattern, the external circuit being capable of measuring the electrical resistance across regions of the deformable nonconductive substrate and determining the degree of deformation thereof.

20 Claims, 7 Drawing Sheets

SIDE A

SIDE B

PRINTED STRETCH SENSOR

CROSS-REFERENCE TO RELATED APPLICATIONS

This application is a continuation of U.S. application Ser. No. 13/566,726, filed Aug. 3, 2012, U.S. Publication Number US-2014-0035603-A1, the disclosure of which is totally incorporated by reference herein.

Reference is made to Copending application Ser. No. 13/182,579, filed Jul. 14, 2011, entitled "Stretchable Ink Composition," with the named inventors Yiliang Wu, Qi Zhang, Ke Zhou, Yu Qi, and Nan-Xing Hu, the disclosure of which is totally incorporated herein by reference.

BACKGROUND

Disclosed herein is a printed stretch sensor that can be prepared by printing methods such as ink jet printing.

Stretch sensors typically come in a one-dimensional form (only stretching across a single axis). By weaving or knitting stretch sensors into a fabric, multiple degrees of freedom can be achieved. Stretch-sensitive material can also be glued onto an elastic surface, but these techniques are labor-intensive and result in limited range of motion. By creating printed stretch sensors on an elastic surface, one can achieve high range of motion, and manufacture is as simple as printing a material onto a surface.

Conductive elastomers are used in applications requiring deformability and electrical conductivity, such as for gaskets used in EMI-shielding. One notable feature of conductive elastomers is that they change conductivity as they are stretched. By measuring the electrical resistance through such a material, one can calculate the degree of stretch.

Conductive stretchable inks are known, as disclosed in, for example, "Inkjet-Printed Stretchable Silver Electrode on Wave Structured Elastomeric Substrate," Seungjun Chung, Jaemyon Lee, Hyunsoo Song, Sangwoo Kim, Jaewook Jeong, and Yongtaek Hong, *Applied Physics Letters*, 98, 153110 (2011) and Copending application Ser. No. 13/182,579, filed Jul. 14, 2011, entitled "Stretchable Ink Composition," with the named inventors Yiliang Wu, Qi Zhang, Ke Zhou, Yu Qi, and Nan-Xing Hu, the disclosures of each of which are totally incorporated herein by reference.

Much of the work related to conductive elastomers has attempted to overcome the challenge of conductivity loss during deformation. In contrast, the articles disclosed herein take advantage of this property.

Accordingly, while known articles and compositions are suitable for their intended purposes, a stretch sensor which stretches in two dimension (i.e., along two axes) that can be prepared by printing a conductive ink in an imagewise pattern onto a deformable nonconductive substrate in such a way that both materials can stretch and return back to their original shape is desirable.

SUMMARY

Disclosed herein is a patterned article comprising: (1) a deformable nonconductive substrate; (2) an imagewise pattern thereon of a conductive stretchable ink; and (3) an external circuit connecting the imagewise pattern, said external circuit being capable of measuring the electrical resistance across regions of the deformable nonconductive substrate and determining the degree of deformation thereof. Also disclosed herein is a patterned article comprising: (1) a deformable nonconductive substrate having a resistivity of at least about $1.8 \times 10^5$ $\Omega$m and an elasticity in the direction of elongation of at least about 0.0008 MPa; (2) an imagewise pattern thereon of a conductive stretchable ink having a conductivity of from about 0.01 µS to about 100 MS and comprising a fluoroelastomer; and (3) an external circuit connecting the imagewise pattern, said external circuit being capable of measuring the electrical resistance across regions of the deformable nonconductive substrate and determining the degree of deformation thereof. Further disclosed herein is a process which comprises: (a) applying to a deformable nonconductive substrate in an imagewise pattern a conductive stretchable ink; (b) connecting the imagewise pattern with an external circuit; and (c) measuring the electrical resistance across regions of the deformable nonconductive substrate and determining the degree of deformation thereof.

DETAILED DESCRIPTION

Figure 1A:
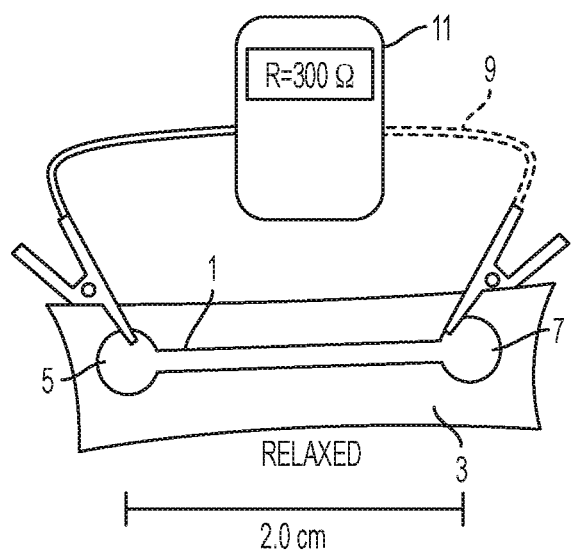
FIGS. 1A and 1B illustrate a first embodiment of the articles and apparatus disclosed herein.

The articles and apparatus disclosed herein comprise conductive inks printed onto nonconductive deformable substrates. By "nonconductive" is meant herein a substrate having a resistivity of in one embodiment at least about $1.8 \times 10^5$ $\Omega$m, in another embodiment at least about 100 M$\Omega$m (100 mega$\Omega$m; $1 \times 10^6$ $\Omega$m), in yet another embodiment at least about 1 G$\Omega$m (1 giga$\Omega$m; $1 \times 10^9$ $\Omega$m), and in still another embodiment at least about 100 G$\Omega$m, with no upper limit on resistivity, although the value can be outside of these ranges.

The substrate is deformable. By "deformable" is meant herein a substrate having high elasticity in the direction of deformation, in one embodiment at least about 0.0008 MPa (megaPascals), in another embodiment at least about 0.0009 MPa, in yet another embodiment at least about 0.001 PMa, in still another embodiment at least about 0.008 MPa, in yet another embodiment at least about 0.009 MPa, and in still another embodiment at least about 0.01 MPa, and in one embodiment no more than about 0.1 MPa, in another embodiment no more than about 0.09 MPa, in yet another embodiment no more than about 0.08 MPa, and in still another embodiment no more than about 0.01 MPa, although the value can be outside of these ranges.

Examples of suitable substrates include (but are not limited to) rubber, such as natural polyisoprene, polybutadiene rubber, chloroprene rubber, neoprene rubber, butyl rubber (copolymer of isobutylene and isoprene), styrene-butadiene rubber, silicon rubber, nitrile rubber (which is a copolymer of butadiene and acrylonitrile), ethylene propylene rubber, ethylene propylene diene rubber, epichlorohydrin rubber, polyacrylic rubber, ethylene-vinyl acetate, polyether block amides, polysulfide rubber, chlorosulfonated polyethylene as HYPALON, or the like. In a specific embodiment, the inks disclosed herein can be printed on a silicon rubber, polyacrylic rubber, butyl rubber, or neoprene rubber substrate and the imaged substrate can be stretched in one axial direction (i.e., along the x-axis, as opposed to both the x-axis and the y-axis) to in one embodiment at least 110%, in another embodiment at least 150%, and in yet another embodiment at least 200%, of the length of its original dimension in one embodiment at least about 50 times, in another embodiment at least about 100 times, and in yet another embodiment at least about 500 times, without exhibiting cracks or delamination.

An imagewise pattern is printed onto the deformable substrate with a conductive stretchable ink. By "conductive is meant herein a conductivity of in one embodiment at least about 0.01 μS (microSiemen), and in another embodiment at least about 0.05 S (Siemen), and in one embodiment no more than about 100 MS (megaSiemens), although the value can be outside of these ranges.

The ink is one suitable for ink jet printing onto the substrate. In one embodiment, the ink composition is a low-viscosity composition. The term "low-viscosity" is used in contrast to conventional high-viscosity inks such as screen printing inks, which tend to have a viscosity of at least 1,000 centipoise (cps). In specific embodiments, the ink disclosed herein has a viscosity of in one embodiment no more than about 100 cps, in another embodiment no more than about 50 cps, and in yet another embodiment no more than about 20 cps, although the viscosity can be outside of these ranges. When used in ink jet printing applications, the ink compositions are generally of a viscosity suitable for use in said ink jet printing processes. For example, for thermal ink jet printing applications, at room temperature (i.e., about 25° C.), the ink viscosity is in one embodiment at least about 1 cps and in one embodiment is no more than about 10 cps, in another embodiment no more than about 7 cps, and in yet another embodiment no more than about 5 cps, although the viscosity can be outside of these ranges. For example, for piezoelectric ink jet printing, at the jetting temperature, the ink viscosity is in one embodiment at least about 2 cps, and in another embodiment at least about 3 cps, and in one embodiment is no more than about 20 cps, in another embodiment no more than about 15 cps, and in yet another embodiment no more than about 10 cps, although the viscosity can be outside of these ranges. The jetting temperature can be as low as about 20 to 25° C., and can be in one embodiment as high as about 90° C., in another embodiment as high as about 60° C., and in yet another embodiment as high as about 40° C., although the jetting temperature can be outside of these ranges.

In one specific embodiment, the ink contains a fluoroelastomer as disclosed in Copending application Ser. No. 13/182,579, the disclosure of which is totally incorporated herein by reference. An elastomer is defined by the *Collins English Dictionary* as any material, such as natural or synthetic rubber, that is able to resume its original shape when a deforming force is removed. A fluoroelastomer, for the purposes of the present disclosure, is a fluoropolymer that behaves according to this definition of an elastomer.

The elastomeric fluoropolymer can be a perfluoropolymer or it can contain atoms other than carbon and fluorine, such as hydrogen, chlorine and other halogens, oxygen, nitrogen, sulfur, silicon, and the like, as well as mixtures thereof. The term "fluoropolymer" is intended to denote any polymer comprising more than 25 percent by weight of recurring monomer units derived from at least one ethylenically unsaturated monomer comprising at least one fluorine atom (hereinafter, fluorinated monomer). When the fluorinated monomer is free of hydrogen atoms and contains other halogen atoms, it is referred to as a per(halo)fluoromonomer. When the fluorinated monomer contains hydrogen atoms, it is referred to as a hydrogen-containing fluorinated monomer.

Examples of common fluorinated monomers include, but are not limited to, tetrafluoroethylene (TFE); $C_3$-$C_8$ perfluoroolefins, such as hexafluoropropene (HFP); $C_2$-$C_8$ hydrogenated monofluoroolefins, such as vinyl fluoride; vinylidene fluoride (VdF); 1,2-difluoroethylene and trifluoroethylene; perfluoroalkylethylenes complying with formula $CH_2=CH-R_{f0}$, in which $R_{f0}$ is a $C_1$-$C_6$ perfluoroalkyl, chloro- and/or bromo- and/or iodo-$C_2$-$C_6$ fluoroolefins, like chlorotrifluoroethylene (CTFE); (per) fluoroalkylvinylethers (PAVE) complying with formula $CF_2=CFOR_{f1}$ in which $R_{f1}$ is a $C_1$-$C_6$ fluoro- or perfluoroalkyl, e.g. $CF_3$, $C_2F_5$, $C_3F_7$; $CF_2=CFOX_0$ (per)fluoro-oxyalkylvinylethers, in which $X_0$ is a $C_1$-$C_{12}$ alkyl, or a $C_1$-$C_{12}$ oxyalkyl, or a $C_1$-$C_{12}$ (per)fluorooxyalkyl having one or more ether groups, like perfluoro-2-propoxy-propyl; (per)fluoromethoxyalkylvinylethers complying with formula $CF_2=CFOCF_2OR_{f2}$ in which $R_{f2}$ is a $C_1$-$C_6$ fluoro- or perfluoroalkyl, e.g. $CF_3$, $C_2F_5$, $C_3F_7$ or a $C_1$-$C_6$ (per)fluorooxyalkyl having one or more ether groups, like —$C_2F_5$—O—$CF_3$; functional (per)fluoroalkylvinylethers complying with formula $CF_2=CFOY_0$, in which $Y_0$ is a $C_1$-$C_{12}$ alkyl or (per)fluoroalkyl, or a $C_1$-$C_{12}$ oxyalkyl, or a $C_1$-$C_{12}$ (per)fluorooxyalkyl having one or more ether groups and $Y_0$ comprising a carboxylic or sulfonic acid group, in its acid, acid halide or salt form; fluorodioxoles, especially perfluorodioxoles; and the like. Copolymers of two or more fluorinated monomers are also possible.

The fluoropolymer can be a copolymer containing fluorinated monomers as well as hydrogenated monomers (a term referring to monomers free of fluorine atoms for the purposes of the present disclosure). Examples of suitable hydrogenated monomers include, but are not limited to, ethylene, propylene, vinyl monomers such as vinyl acetate, acrylic monomers, such as methyl methacrylate, acrylic acid, methacrylic acid, ethylacrylate, n-butylacrylate, hydroxypropylacrylate, (hydroxy)ethylhexylacrylate, and hydroxyethyl acrylate, and the like, styrene monomers, like styrene and p-methylstyrene, vinyl ethers, such as propylvinylether, cyclohexylvinylether, vinyl-4-hydroxybutylether, unsaturated carboxylic acids, such as vinylacetic acid, and the like, as well as mixtures thereof.

Some specific examples of suitable fluoroelastomers include (but are not limited to) fluoro rubbers of the polymethylene type that use vinylidene fluoride as a comonomer and have substituent fluoro, alkyl, perfluoroalkyl, or perfluoroalkyoxy groups in the polymer chain, with or without a curesite monomer, such as copolymers of vinylidene fluoride and hexafluoropropylene; terpolymers of vinylidene fluoride, hexafluoropropylene, and tetrafluoroethylene; copolymers of vinylidene fluoride and (per)fluoromethoxyalkylvinylethers; terpolymers of vinylidene fluoride, hexafluoropropylene, and polyperfluoromethylvinylether; terpolymers of vinylidene fluoride, tetrafluoroethylene, and a fluorinated vinyl ether; terpolymer of vinylidene fluoride, tetrafluoroethylene, and propylene; tetrapolymers of vinylidene fluoride, hexafluoropropylene, tetrafluoroethylene, and polyperfluoromethylvinylether; terpolymers of tetrafluoroethylene, propylene, and vinylidene fluoride; pentapolymers of tetrafluoroethylene, hexafluoroethylene, vinylidene fluoride, ethylene, and polyperfluoromethylvinylether; perfluoro rubbers of the polymethylene type having all substituent groups on the polymer chain either fluoro, perfluoroalkyl, or perfluoroalkyoxyl groups; fluoro rubbers of the polymethylene type containing one or more of the monomeric alkyl, perfluoroalkyl, and/or perfluoroalkoxy groups with or without a curesite monomer; and the like, as well as mixtures thereof. One specific example of a suitable fluoroelastomer is commercially available as TECNOFLON® TN latex from Solvay Solexis. Other commercially available fluoroelastomers such as VITON® from DuPont, DYNEON™ from 3M, AFLAS®, DAI-EL™ from Daikin, and the like can be used as well.

In one embodiment, the fluoroelastomer has a fluorine content of at least about 5 weight %, in another embodiment at least about 10 weight %, and in yet another embodiment at least about 30 weight %, and in one embodiment no more than about 76 weight % (perfluoroelastomer), in another embodiment no more than about 70 weight %, and in yet another embodiment no more than about 68 weight %, although the fluorine content can be outside of these ranges.

In one embodiment, the fluoroelastomer has a tensile strength of at least about 3 MPa, in another embodiment at least about 4 MPa, and in yet another embodiment at least about 7 MPa, and in one embodiment no more than about 25 MPa, in another embodiment no more than about 20 MPa, and in yet another embodiment no more than about 18 MPa, as measured by ASTM D412C, although the tensile strength can be outside of these ranges.

In one embodiment, the fluoroelastomer has an elongation at break of at least about 150%, in another embodiment at least about 200%, and in yet another embodiment at least about 400%, and in one embodiment no more than about 1100%, in another embodiment no more than about 1000%, and in yet another embodiment no more than about 800%, as measured by ASTM D412C, although the elongation at break can be outside of these ranges.

In one embodiment, the fluoroelastomer has a hardness (Shore A) value of at least about 20, in another embodiment at least about 30, and in yet another embodiment at least about 40, and in one embodiment no more than about 90, in another embodiment no more than about 85, and in yet another embodiment no more than about 80, as measured by ASTM 2240, although the hardness can be outside of these ranges.

In one embodiment, the fluoroelastomer has a glass transition temperature of at least about −70° C., in another embodiment at least about −50° C., and in yet another embodiment at least about −40° C., and in one embodiment no more than about 25° C., in another embodiment no more than about 0° C., and in yet another embodiment no more than about −10° C., although the Tg can be outside of these ranges.

The fluoroelastomer is present in the ink in any desired or effective amount, in one embodiment at least about 0.1 percent by weight of the ink, in another embodiment at least about 1 percent by weight of the ink, and in yet another embodiment at least about 2 percent by weight of the ink, and in one embodiment no more than about 25 percent by weight of the ink, in another embodiment no more than about 20 percent by weight of the ink, and in yet another embodiment no more than about 15 percent by weight of the ink, although the amount can be outside of these ranges.

When the inks contain a fluoroelastomer, the inks disclosed herein also contain a surfactant. Any surfactant that forms an emulsion of the fluoroelastomer in the ink can be employed. Examples of suitable surfactants include anionic surfactants, cationic surfactants, nonionic surfactants, zwitterionic surfactants, and the like, as well as mixtures thereof. Examples of suitable surfactants include alkyl polyethylene oxides, alkyl phenyl polyethylene oxides, polyethylene oxide block copolymers, acetylenic polyethylene oxides, polyethylene oxide (di)esters, polyethylene oxide amines, protonated polyethylene oxide amines, protonated polyethylene oxide amides, dimethicone copolyols, substituted amine oxides, and the like, with specific examples including primary, secondary, and tertiary amine salt compounds such as hydrochloric acid salts, acetic acid salts of laurylamine, coconut amine, stearylamine, rosin amine; quaternary ammonium salt type compounds such as lauryltrimethylammonium chloride, cetyltrimethylammonium chloride, benzyltributylammonium chloride, benzalkonium chloride, etc.; pyridinium salty type compounds such as cetylpyridinium chloride, cetylpyridinium bromide, etc.; nonionic surfactant such as polyoxyethylene alkyl ethers, polyoxyethylene alkyl esters, acetylene alcohols, acetylene glycols; and other surfactants such as 2-heptadecenyl-hydroxyethylimidazoline, dihydroxyethylstearylamine, stearyldimethylbetaine, and lauryldihydroxyethylbetaine; fluorosurfactants; and the like, as well as mixtures thereof. Additional examples of nonionic surfactants include polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, available from Rhone-Poulenc as IGEPAL CA-210™ IGEPAL CA-520™, IGEPAL CA-720™, IGEPAL CO-890™, IGEPAL CO-720™, IGEPAL CO-290™, IGEPAL CA-210™, ANTAROX 890™, and ANTAROX 897™. Other examples of suitable nonionic surfactants include a block copolymer of polyethylene oxide and polypropylene oxide, including those commercially available as SYNPERONIC PE/F, such as SYNPERONIC PE/F 108. Other examples of suitable anionic surfactants include sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid available from Aldrich, NEOGEN R™, NEOGEN SC™ available from Daiichi Kogyo Seiyaku, combinations thereof, and the like. Other examples of suitable anionic surfactants include DOWFAX™ 2A1, an alkyldiphenyloxide disulfonate from Dow Chemical Company, and/or TAYCA POWER BN2060 from Tayca Corporation (Japan), which are branched sodium dodecyl benzene sulfonates. Other examples of suitable cationic surfactants, which are usually positively charged, include alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quaternized polyoxyethylalkylamines, dodecylbenzyl triethyl ammonium chloride, MIRAPOL™ and ALKAQUAT™, available from Alkaril Chemical Company, SANIZOL™ (benzalkonium chloride), available from Kao Chemicals, and the like, as well as mixtures thereof. Mixtures of any two or more surfactants can be used. The surfactant is present in any desired or effective amount, in one embodiment at least about 0.01 percent by weight of the ink, and in one embodiment no more than about 5 percent by weight of the ink, although the amount can be outside of these ranges.

The ink further contains a conductive component. Any desired or effective conductive component can be employed. Examples include (but are not limited to) carbon black, polypyrrole, polyacetylene, polyaniline, polyphenylene vinylene, polythiophene, polyphenylene sulfide, graphene, silver nanoparticles, copper nanoparticles, or the like, as well as mixtures thereof.

In one specific embodiment, the ink is of a material that contains substantially no silver nanoparticles. In another specific embodiment, the ink is of a material that contains substantially no copper nanoparticles. By "nanoparticles" is meant particles having an average particle diameter of no more than about 100 nm.

The conductive component is present in the ink in any desired or effective amount, in one embodiment at least about 52 percent by volume of the dried or cured ink, in another embodiment at least about 56 percent by volume of the dried or cured ink, and in yet another embodiment at least about 61 percent by volume of the dried or cured ink, and in one embodiment no more than about 74 percent by volume of the dried or cured ink, in another embodiment no more than about 70 percent by volume of the dried or cured ink, and in yet another embodiment no more than about 65 percent by volume of the dried or cured ink, although the amount can be outside of these ranges.

The ink composition can further comprise crosslinkers. In embodiments, the crosslinker is an organoamine, a dihydroxy aromatic compound, a peroxide, a metal oxide, or the like, as well as mixtures thereof. Crosslinking can further enhance the physical properties of the images generated from the ink composition. The crosslinker can be present in any desired or effective amount, in one embodiment at least about 0.1 percent by weight of the ink, in another embodiment at least about 1 percent by weight of the ink, and in yet another embodiment at least about 5 percent by weight of the ink, and in one embodiment no more than about 20 percent by weight of the ink, in another embodiment no more than about 15 percent by weight of the ink, and in yet another embodiment no more than about 10 percent by weight of the ink, although the amount can be outside of these ranges.

The conductive ink is printed onto the deformable substrate in an image pattern. The ink compositions can be used in a process which entails incorporating the ink composition into an ink jet printing apparatus and causing droplets of the ink to be ejected in an imagewise pattern onto a substrate. In a specific embodiment, the printing apparatus employs a thermal ink jet process wherein the ink in the nozzles is selectively heated in an imagewise pattern, thereby causing droplets of the ink to be ejected in imagewise pattern. In another embodiment, the printing apparatus employs an acoustic ink jet process wherein droplets of the ink are caused to be ejected in imagewise pattern by acoustic beams. In yet another embodiment, the printing apparatus employs a piezoelectric ink jet process, wherein droplets of the ink are caused to be ejected in imagewise pattern by oscillations of piezoelectric vibrating elements.

In one embodiment, the inks disclosed herein can be printed on a rubber substrate, such as natural polyisoprene, polybutadiene rubber, chloroprene rubber, neoprene rubber, butyl rubber (copolymer of isobutylene and isoprene), styrene-butadiene rubber, silicon rubber, nitrile rubber (which is a copolymer of butadiene and acrylonitrile), ethylene propylene rubber, ethylene propylene diene rubber, epichlorohydrin rubber, polyacrylic rubber, ethylene-vinyl acetate, polyether block amides, polysulfide rubber, chlorosulfonated polyethylene as HYPALON, or the like. In a specific embodiment, the inks disclosed herein can be printed on a silicon rubber, polyacrylic rubber, butyl rubber, or neoprene rubber substrate and the imaged substrate can be stretched in one axial direction (i.e., along the x-axis, as opposed to both the x-axis and the y-axis) to in one embodiment at least 110%, in another embodiment at least 150%, and in yet another embodiment at least 200%, of the length of its original dimension in one embodiment at least about 50 times, in another embodiment at least about 100 times, and in yet another embodiment at least about 500 times, without exhibiting cracks or delamination.

In one embodiment, the inks disclosed herein can be printed on a silicon rubber, polyacrylic rubber, butyl rubber, or neoprene rubber substrate and the imaged substrate can be submerged in water for in one embodiment at least about 1 day, in another embodiment for at least about 1 week, and in yet another embodiment for at least about 1 month, without exhibiting damage to the imagewise pattern.

In a specific embodiment, the images generated with the inks disclosed herein are highly water-resistant. In one embodiment, images generated with the inks exhibit a water droplet contact angle of at least about 80°, in another embodiment at least about 90°, and in yet another embodiment at least about 95°, although the contact angle can be outside of these ranges. The water-resistant characteristic renders the ink disclosed herein suitable for outdoor applications or printing on water-related products such vehicle wrap, swimming suits, and the like.

In a specific embodiment, the images generated with the inks disclosed herein have a good chemical resistance. For example, they can exhibit good to excellent resistance toward alcohols, acetic acid, acetamide, allyl bromide, allyl chloride, benzoyl chloride, ethers, esters, hydrocarbons, blood, salt solutions, and the like.

In one embodiment, the images generated with the inks disclosed herein have a tensile strength of at least about 3 MPa, in another embodiment at least about 4 MPa, and in yet another embodiment at least about 8 MPa, and in one embodiment no more than about 25 MPa, in another embodiment no more than about 20 MPa, and in yet another embodiment no more than about 18 MPa, as measured by ASTM D412C, although the tensile strength can be outside of these ranges.

In one embodiment, the images generated with the inks disclosed herein have an elongation at break of at least about 150%, in another embodiment at least about 200%, and in yet another embodiment at least about 400%, and in one embodiment no more than about 1000%, in another embodiment no more than about 800%, and in yet another embodiment no more than about 700%, as measured by ASTM D412C, although the elongation at break can be outside of these ranges. Generally, the images have a larger elongation at break than that of the deformable substrate.

In one embodiment, the images generated with the inks disclosed herein have a hardness (Shore A) value of at least about 20, in another embodiment at least about 30, and in yet another embodiment at least about 40, and in one embodiment no more than about 100, in another embodiment no more than about 90, and in yet another embodiment no more than about 85, as measured by ASTM 2240, although the hardness can be outside of these ranges.

Figure 1B:
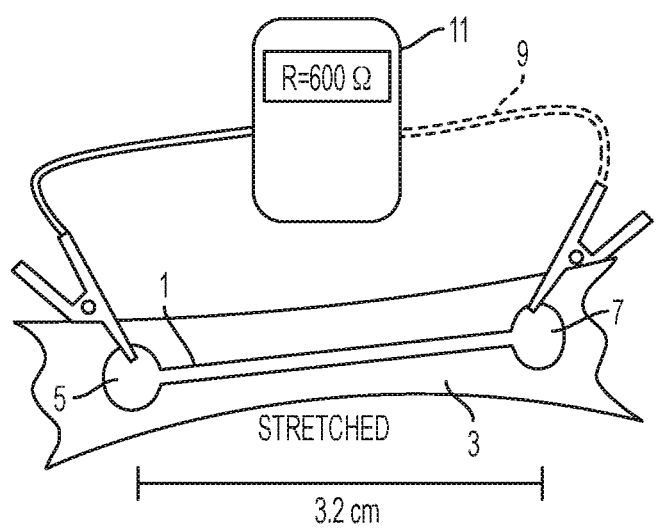
Figure 2A:
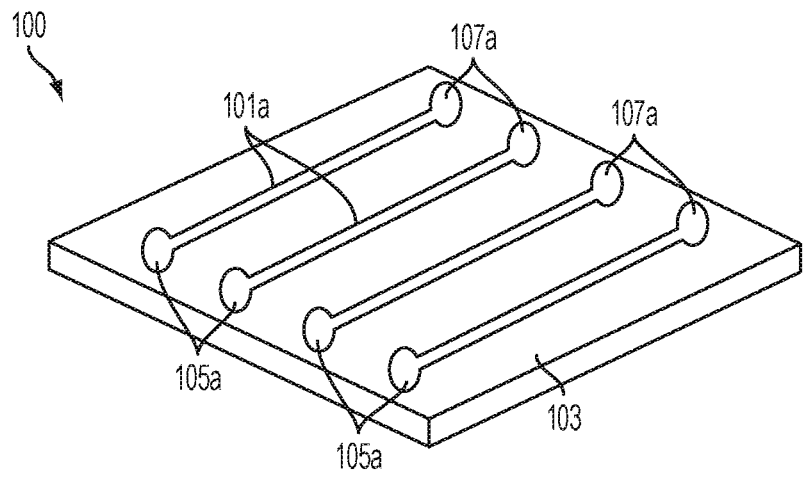
FIGS. 2A and 2B, 3, 4, and 5A, 5B, and 5C illustrate a second embodiment of the articles and apparatus disclosed herein wherein a pressure-sensitive touch sensor is demonstrated.
Figure 2B:
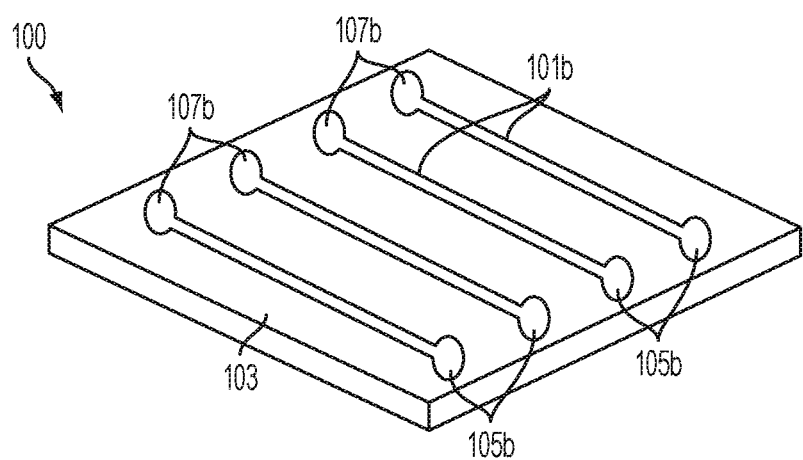
Figure 3:
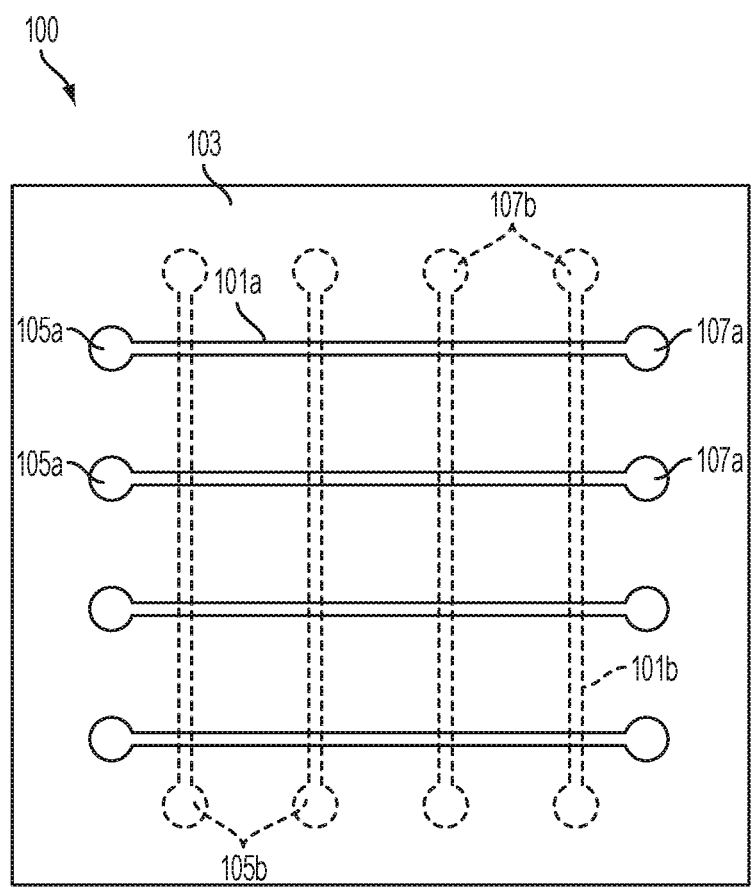

An external circuit connects the imagewise pattern. The external circuit is capable of measuring the electrical resistance across regions of the deformable nonconductive substrate and determining the degree of deformation thereof. In its simplest embodiment, illustrated in FIGS. 1A and 1B, a single line 1 of the conductive stretchable ink is printed onto the deformable nonconductive substrate 3 and the distal ends 5 and 7 of line 1 are connected with an external circuit 9 and ohmmeter 11 to measure the resistivity across line 1. As shown on the "relaxed" image and substrate in FIG. 1A, the resistivity of line 1 is lower than it is on the "stretched" image and substrate in FIG. 1B. The degree of resistivity for the specific ink material can be correlated to the degree of stretch. The correlation between degree of stretch and resistivity will vary depending on the selected materials and formulation, and can be determined experimentally for the selected article.

Figure 4:
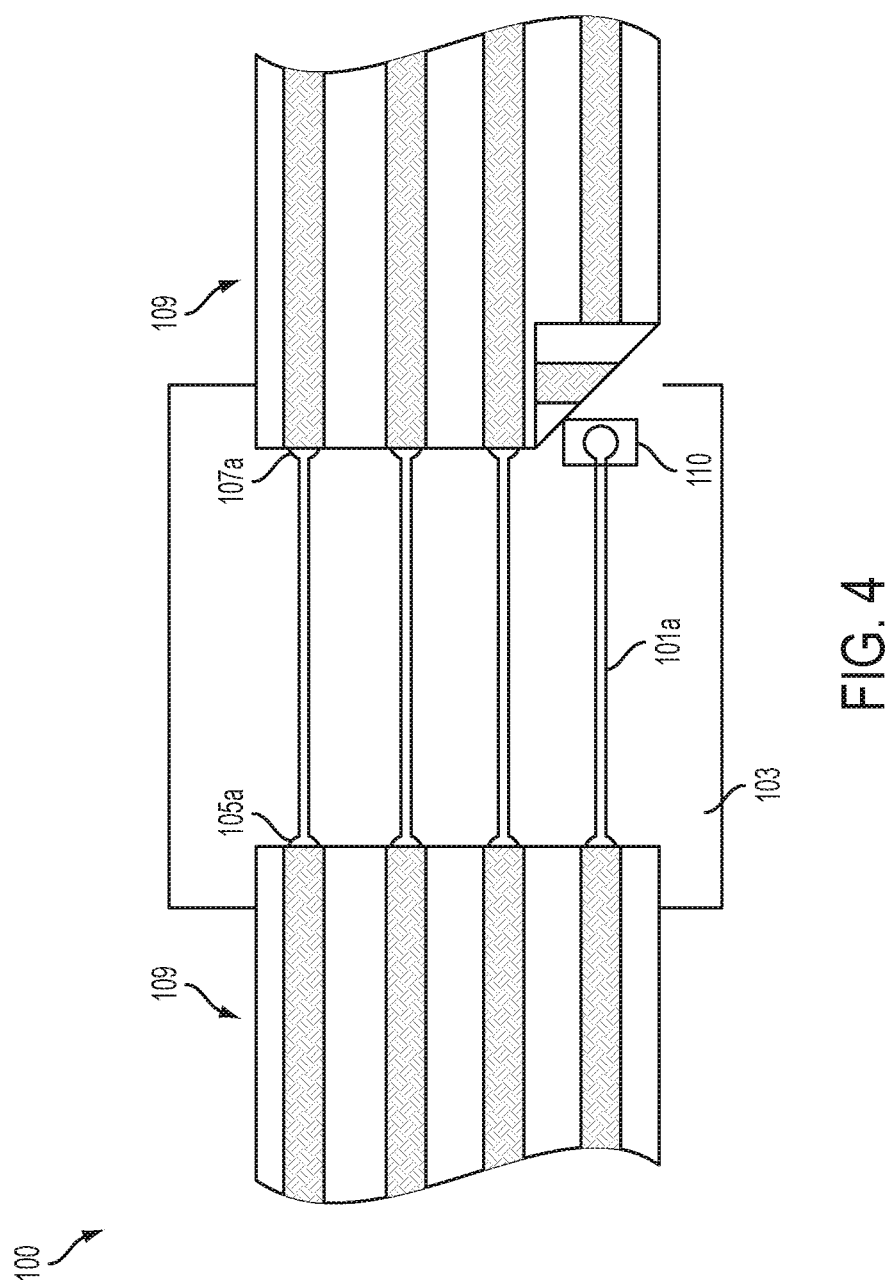

In another embodiment, as illustrated in FIGS. 2A and 2B, 3, 4, and 5A, 5B, and 5C, a touch sensitive array 100 is provided that can pinpoint the precise location of a touch on a surface. On opposite sides A and B of a deformable nonconductive substrate 103 are printed lines 101 (shown as 101a on surface A and 101b on surface B) of a conductive stretchable ink in alternating orientations so that the resulting configuration forms a grid. Lines 101a do not cross each other. Lines 101b do not cross each other. At least some of lines 101a cross at least some of lines 101b. In one specific embodiment, the grid lines 101a are substantially perpendicular to lines 101b. Opposite sides are used so that the electrically conductive traces do not cross one another and form a short. At each end of the conductive lines 101 are enlarged pads 105 and 107 (shown as 105a on surface A and 105b on surface B, and 107a on surface A and 107b on surface B) to facilitate electrical connections. As shown in FIG. 4, permanent connections can be made by securely gluing on flexible ribbon cables 109 with conductive adhesive 110.

Figure 5A:
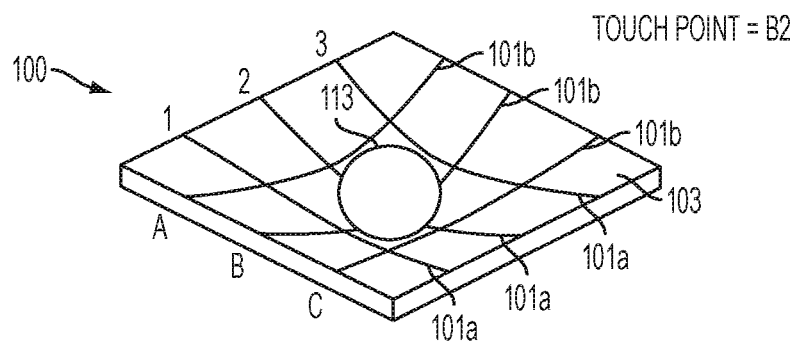
Figure 5B:
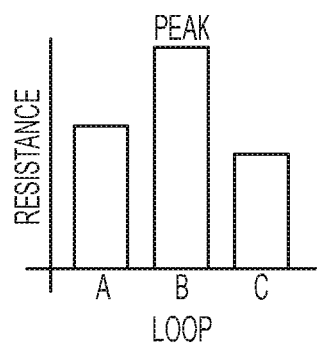
Figure 5C:
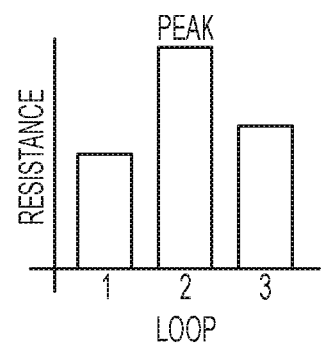

Each line of printed conductive stretchable ink 101 is configured as a loop in a resistance measuring circuit. As shown in FIG. 5A, a touch is taking place, depicted by sphere 113 deforming the deformable nonconductive substrate 103. In this state, one can sample the resistance in each loop and determine which loops are experiencing peak resistance. These loops will be the ones intersecting with the touch location. Using two sets of loops, one for the X-coordinate and one for the Y-coordinate, one can pinpoint the exact location of the touch as indicated by the plots shown in FIGS. 5B and 5C. The loops are attached to an external circuit that measures resistance and processes the data to come up with a derived value such as the mass of an object or a value that can be compared with values from adjacent loops to determine the locality of maximum deformation. Such a material can be stretched across a springy foam backing to create a fingertip-like device that will register touches, when deformed, and then return back to its original shape and resistance signature, when not. This device can be used, for example, in industrial robotics applications, where a sensitive touch response would allow equipment to operate more effectively. For example, in applications wherein a robot lifts an article, this device can be employed to detect whether the robot is holding the article securely or not.

Figure 6:
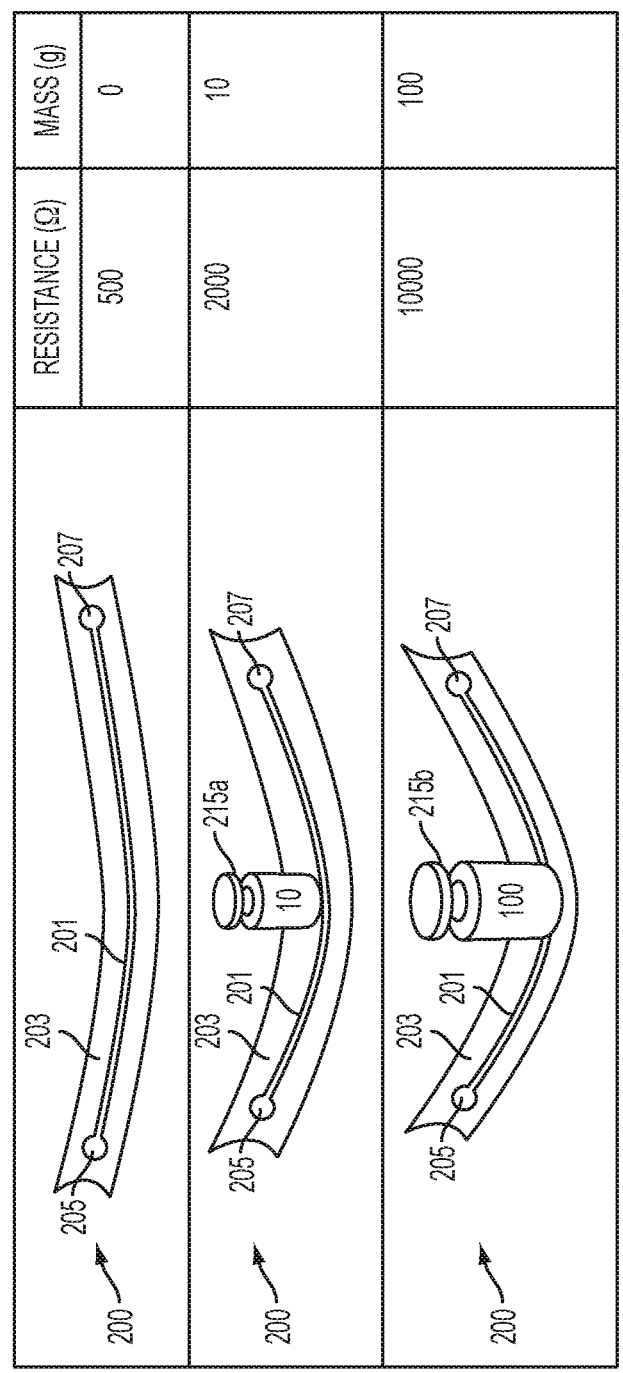
FIGS. 6 and 7A and 7B illustrate a third embodiment of the articles and apparatus disclosed herein wherein a pressure-sensitive weighing device is demonstrated.
Figure 7A:
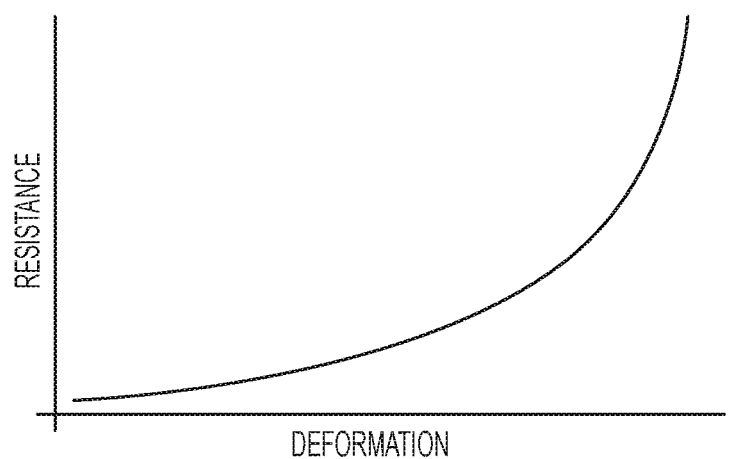
Figure 7B:
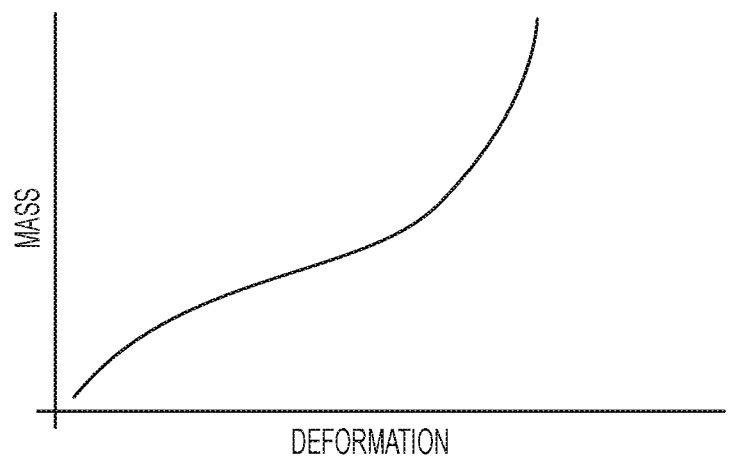

In yet another embodiment, as illustrated in FIGS. 6 and 7A and 7B, a printed weighing device 200 is provided. On a deformable nonconductive substrate 203 is printed one or more lines 201 of a conductive stretchable ink. The term "lines" here includes straight lines as well as wavy lines, curves, or the like, provided that the printed article provides measurable, continuous changes in resistance when deformed. At each end of the conductive line or lines 201 are enlarged pads 205 and 207 to facilitate electrical connections (not shown). Circuitry can be completed as shown in FIG. 1. Articles of varying mass 215a and 215b are placed on the deformable nonconductive substrate 203 printed with a pattern 201 of conductive material, the conductivity of which decreases with the degree of stretch, and the conductive material 201 stretches to a different degree with different amounts of mass. Likewise, the measured resistance through the conductive pattern will increase in a repeatable way relative to the degree of stretch so that a particular mass will correspond to a specific resistance measurement, and one can deduce the mass of an object by measuring the resistance through the conductive printed material. The correlation between degree of stretch and resistivity will vary depending on the selected materials and formulation, and can be determined experimentally for the selected article.

Specific embodiments will now be described in detail. These examples are intended to be illustrative, and the claims are not limited to the materials, conditions, or process parameters set forth in these embodiments. All parts and percentages are by weight unless otherwise indicated.

Example I

A fluoroelastomer emulsion (TECNOFLON® TN latex, Solvay Solexis Inc., West Deptford, N.J., solids content 64.91 wt %) is mixed with carbon black (solid contents 19.96%, also containing sodium dodecyl benzene sulfonate surfactant in an amount of 2 wt. %) to form a homogenous dispersion in which the solids content contains 5 wt. % pigment. The mixture is first diluted with distilled water until a suitable viscosity (~5 cps) is achieved for ink jet printing. Ethylene glycol is then added into the diluted mixture at a 1:9 ratio (1 part by weight ethylene glycol per 9 parts by weight mixture) to prevent the dispersion from drying in the nozzle. This jettable ink is printed on a natural latex rubber substrate (latex glove) using a DMP-2800 ink jet printer (Fuji Film Dimatix, Santa Clara, Calif.) equipped with 10 pL cartridges (DMC-11610). After printing, the ink solvents are dried at 60° C. for about 5 min. It is believed that the images thus generated will be able to be stretched in both directions up to 500% (which is the limit of the substrate), and that after hundreds of stretch-relaxation cycles, the images will stay firmly on the substrate without any damage such as cracks or de-lamination. It is also believed that the printed images, when tested against water exposure by brushing them under water, will exhibit no visible damage.

Example II

The process of Example I is repeated except that a polydimethylsiloxane (PDMS) silicon rubber substrate is used. The PDMS substrate is made in the laboratory using Dow Corning SYLGARD 184 kit. It is believed that similar results will be obtained, and that the printed image will be able to be stretched up to 200% (limit of the PDMS substrate) for hundreds of cycles without visible damage.

Example III

The process of Example I is repeated except that another fluoroelastomer, DYNEON™ FX 10180 fluoroelastomer (terpolymer latex of vinylidene fluoride, hexafluoropropylene, and tetrafluoroethylene) is used instead of the TECNOFLON® TN. It is believe that similar results will be observed.

Example IV

The process of Example I is repeated except that another conductive pigment, polypyrrole, is used instead of the carbon black. It is believe that similar results will be observed.

Example V

The process of Example I is repeated except that another conductive pigment, polyacetylene, is used instead of the carbon black. It is believe that similar results will be observed.

Example VI

The process of Example I is repeated except that another conductive pigment, polyphenylene sulfide, is used instead of the carbon black. It is believe that similar results will be observed.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A patterned article comprising:
   (1) an elastomeric nonconductive substrate having a resistivity of at least $1.8 \times 10^5$ Ωm and an elasticity in the direction of elongation of at least 0.0008 MPa;
   (2) an imagewise pattern comprising an electrically conductive stretchable ink on the substrate; and
   (3) an external circuit electrically connected to the imagewise pattern, wherein the external circuit measures electrical resistance across a predetermined region of the elastomeric nonconductive substrate, wherein a user touching a surface portion of the elastomeric nonconductive substrate causes a thus-touched surface portion of the elastomeric nonconductive substrate to deform into a sphere, enabling the thus-touched substrate surface portion to function as a touch sensor.

2. An article according to claim 1, wherein the elastomeric nonconductive substrate is selected from neoprene rubber, butyl rubber, styrene-butadiene rubber, silicon rubber, nitrile rubber, ethylene propylene rubber, ethylene propylene diene rubber, epichlorohydrin rubber, polyacrylic rubber, ethylene-vinyl acetate, polyether block amides, polysulfide rubber, chlorosulfonated polyethylene, or mixtures thereof.

3. An article according to claim 1, wherein the electrically conductive stretchable ink includes a fluoroelastomer.

4. An article according to claim 1, wherein the electrically conductive stretchable ink includes an electrically conductive pigment selected from carbon black, polypyrrole, polyacetylene, polyaniline, polyphenylene vinylene, polythiophene, polyphenylene sulfide, graphene, silver nanoparticles, copper nanoparticles, or mixtures thereof.

5. An article according to claim 1, wherein the imagewise pattern further comprises:
   (a) a first set of at least two non-crossing lines of an electrically conductive stretchable ink on a first surface of the elastomeric nonconductive substrate; and
   (b) a second set of at least two non-crossing lines of an electrically conductive stretchable ink on a second surface of the elastomeric nonconductive substrate;
   wherein at least one of the first set of lines on the first surface of the elastomeric nonconductive substrate cross at least one of the second set of lines on the second surface of the elastomeric nonconductive substrate; and
   wherein the external circuit connected to the imagewise pattern enables determination of the location of the thus-touched surface portion of the elastomeric nonconductive substrate functioning as the touch sensor.

6. An article according to claim 5, wherein the elastomeric substrate is selected from neoprene rubber, butyl rubber, styrene-butadiene rubber, silicon rubber, nitrile rubber, ethylene propylene rubber, ethylene propylene diene rubber, epichlorohydrin rubber, polyacrylic rubber, ethylene-vinyl acetate, polyether block amides, polysulfide rubber, chlorosulfonated polyethylene, or mixtures thereof.

7. An article according to claim 5, wherein the electrically conductive stretchable ink on the first or second surface of the elastomeric nonconductive substrate includes a fluoroelastomer.

8. An article according to claim 5, wherein the electrically conductive stretchable ink on the first or second surface of the elastomeric nonconductive substrate includes an electrically conductive pigment selected from carbon black, polypyrrole, polyacetylene, polyaniline, polyphenylene vinylene, polythiophene, polyphenylene sulfide, graphene, silver nanoparticles, copper nanoparticles, or mixtures thereof.

9. An article according to claim 1, wherein the electrically conductive stretchable ink has a conductivity of from about 0.010 μS to 100 MS and comprises a fluoroelastomer.

10. An article according to claim 1, wherein the elastomeric nonconductive substrate has a resistivity of at least 100 MΩm; or
    wherein the elastomeric nonconductive substrate has a resistivity of at least 1 GΩm; or
    wherein the elastomeric nonconductive substrate has a resistivity of at least 100 GΩm.

11. An article according to claim 1, wherein the elastomeric nonconductive substrate has an elasticity in the direction of deformation at least 0.001 MPa.

12. An article according to claim 1, wherein the elastomeric nonconductive substrate has an elasticity in the direction of deformation at least 0.01 MPa.

13. An article according to claim 1,
    wherein the elastomeric nonconductive substrate is selected from the group consisting of silicon rubber, polyacrylic rubber, butyl rubber, and neoprene rubber;
    wherein the imagewise pattern comprising an electrically conductive ink on the substrate is an imaged substrate; and
    wherein the imaged substrate can be stretched in one axial direction to at least 110% at least 50 times without exhibiting cracks or delamination.

14. An article according to claim 1,
    wherein the elastomeric nonconductive substrate is selected from the group consisting of silicon rubber, polyacrylic rubber, butyl rubber, and neoprene rubber;
    wherein the imagewise pattern comprising an electrically conductive ink on the substrate is an imaged substrate; and
    wherein the imaged substrate can be stretched in one axial direction to at least 150% at least 50 times without exhibiting cracks or delamination.

15. An article according to claim 1, wherein the electrically conductive stretchable ink includes a fluoroelastomer; and
    wherein the fluoroelastomer has a tensile strength of at least 3 MPa.

16. An article according to claim 1, wherein the electrically conductive stretchable ink includes a fluoroelastomer; and
    wherein the fluoroelastomer has an elongation at break of at least 150%.

17. An article according to claim 1, wherein the electrically conductive stretchable ink is a material that contains substantially no silver nanoparticles.

18. An article according to claim 1, wherein the electrically conductive stretchable ink is a material that contains substantially no copper nanoparticles.

19. An article according to claim 1, wherein the imagewise pattern comprising an electrically conductive stretchable ink has a tensile strength of at least 3 MPa; or
   wherein the imagewise pattern comprising an electrically conductive stretchable ink has a tensile strength of at least 8 MPa.

20. An article according to claim 1, wherein the imagewise pattern comprises at least one loop in a resistance measuring circuit;
   wherein by sampling the resistance in each loop it is determined which loops are experiencing peak resistance; and
   wherein by using two sets of loops, one for the X-coordinate and one for the Y-coordinate, one can pinpoint the exact location of the touch.

* * * * *